(12) United States Patent
Genese

(10) Patent No.: US 6,402,726 B1
(45) Date of Patent: Jun. 11, 2002

(54) CATHETER MOVEMENT CONTROL DEVICE AND METHOD

(75) Inventor: Joseph N. Genese, Covington, GA (US)

(73) Assignee: Medical Technologies of Georgia, Inc., Decatur, GA (US)

( * ) Notice: Subject to any disclaimer, the term of this patent is extended or adjusted under 35 U.S.C. 154(b) by 0 days.

(21) Appl. No.: 09/810,356

(22) Filed: Mar. 19, 2001

(51) Int. Cl.⁷ .............................................. A61M 3/00
(52) U.S. Cl. ...................... 604/328; 604/346; 604/350; 604/349; 251/4; 251/6; 251/7; 251/8; 251/9
(58) Field of Search ................................. 604/327, 328, 604/346, 347, 349, 350, 394; 251/4, 6–9

(56) References Cited

U.S. PATENT DOCUMENTS

| | | |
|---|---|---|
| 2,329,360 A | 9/1943 | Salfisberg |
| 2,552,870 A | 5/1951 | Scherer |
| 2,856,932 A | 10/1958 | Griffitts |
| 3,035,691 A | 5/1962 | Rasmussen |
| 3,185,179 A | 5/1965 | Harautuneian |
| 3,268,203 A | 8/1966 | Gilmont et al. |
| 3,345,988 A | 10/1967 | Vitello |
| 3,481,367 A | 12/1969 | Deuschle |
| 3,556,294 A | 1/1971 | Walck, III et al. |
| 3,642,126 A | 2/1972 | Kurtz et al. |
| 3,648,701 A * | 3/1972 | Botts .......................... 128/321 |
| 3,648,704 A | 3/1972 | Jackson |
| 3,847,370 A * | 11/1974 | Engelher ....................... 251/6 |
| 3,910,410 A | 10/1975 | Shaw |
| 3,934,721 A | 1/1976 | Juster et al. |
| 3,967,728 A | 7/1976 | Gordon et al. |
| 4,140,127 A | 2/1979 | Cianci et al. |
| 4,164,223 A * | 8/1979 | Munib .......................... 128/321 |
| 4,204,527 A | 5/1980 | Wu et al. |
| 4,211,323 A | 7/1980 | Olsen |
| 4,230,115 A | 10/1980 | Walz, Jr. et al. |
| 4,246,909 A | 1/1981 | Wu et al. |
| 4,269,310 A | 5/1981 | Uson |
| 4,285,492 A * | 8/1981 | Bujan ............................. 251/9 |
| 4,421,509 A | 12/1983 | Schneider et al. |
| D273,709 S | 5/1984 | Schneider |
| 4,460,362 A | 7/1984 | Bates |
| 4,540,156 A | 9/1985 | Cross |
| 4,560,378 A * | 12/1985 | Weiland ....................... 604/83 |
| 4,580,573 A * | 4/1986 | Quinn ......................... 128/657 |
| 4,585,435 A | 4/1986 | Vaillancourt |
| 4,652,259 A | 3/1987 | O'Neill |

(List continued on next page.)

FOREIGN PATENT DOCUMENTS

| | | |
|---|---|---|
| GB | 642523 | 9/1950 |
| WO | WO 98/06642 | 2/1998 |

OTHER PUBLICATIONS

Astra Tech "LoFric Hydro Kit", 4 pages (undated); commercially available for several years.
Color plast "Easicath" set, 2 pages (undated); commercially available for several years.
*Drawings of prior art device of inventor Robert L. Wilcox—4 pages. Now pending patent application ser. No.____;filed simultaneously herewith.

*Primary Examiner*—John G. Weiss
*Assistant Examiner*—Michael Bogart

(57) ABSTRACT

A catheter movement control device is presented having therein a resilient biasing member and a tube gripper which mount on a catheter tube. The biasing member and tube gripper are contained within a housing having a shoulder proximate the catheter tube. As the catheter tube is free to move in a forward direction through the housing, upon attempted rearward movement the biasing member engages the tube gripper causing it to pivot against a shoulder within the housing. Upon pivoting the tube gripper tightly engages the catheter tube preventing any further rearward movement of the catheter tube.

14 Claims, 3 Drawing Sheets

U.S. PATENT DOCUMENTS

| | | | |
|---|---|---|---|
| 4,660,802 A | * | 4/1987 | Oscarsson .................. 251/9 |
| 4,673,161 A | * | 6/1987 | Flynn et al. ................ 251/10 |
| 4,802,650 A | * | 2/1989 | Stricker .................... 251/117 |
| 4,869,457 A | * | 9/1989 | Ewerlof ..................... 251/6 |
| 4,911,399 A | * | 3/1990 | Green ....................... 251/6 |
| 4,919,389 A | | 4/1990 | Hoekwater et al. |
| 5,035,399 A | * | 7/1991 | Rantanen-Lee ............ 251/10 |
| 5,147,341 A | | 9/1992 | Starke |
| 5,172,854 A | | 12/1992 | Epstein et al. |
| 5,209,726 A | | 5/1993 | Goosen |
| 5,226,530 A | | 7/1993 | Golden |
| 5,318,546 A | * | 6/1994 | Bierman .................... 604/250 |
| 5,338,313 A | * | 8/1994 | Mollenauer et al. ....... 604/249 |
| 5,514,109 A | * | 5/1996 | Mollenauer et al. ....... 604/249 |
| 5,522,516 A | * | 6/1996 | Duggal et al. ............. 215/11.4 |
| 5,667,084 A | * | 9/1997 | Duggal et al. ............. 215/11.4 |
| 5,935,122 A | * | 8/1999 | Fourkas et al. ............ 604/523 |
| 6,168,577 B1 | * | 1/2001 | Niederjohn et al. ........ 604/23 |

* cited by examiner

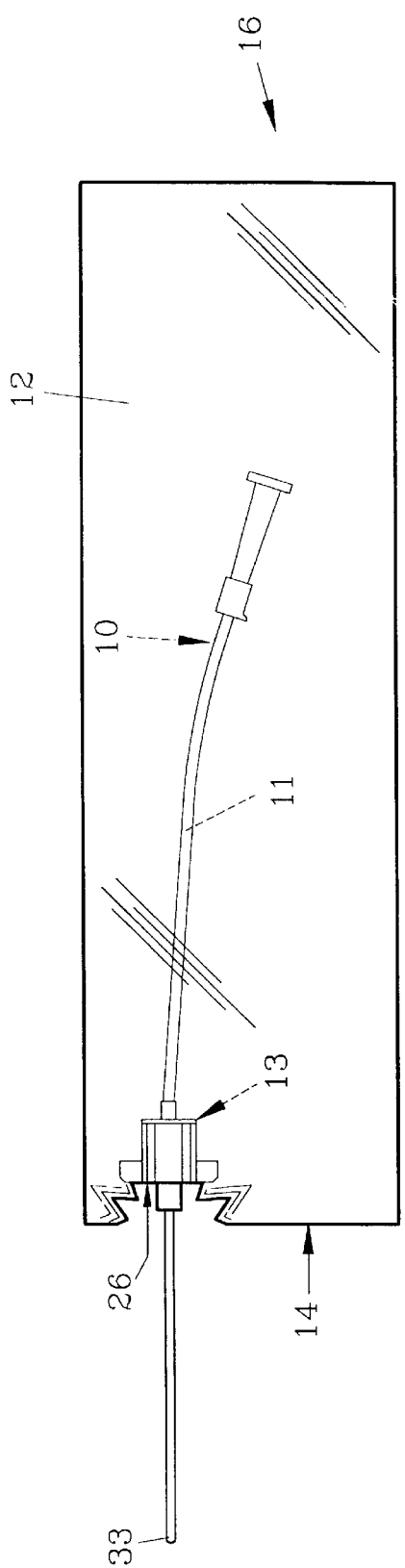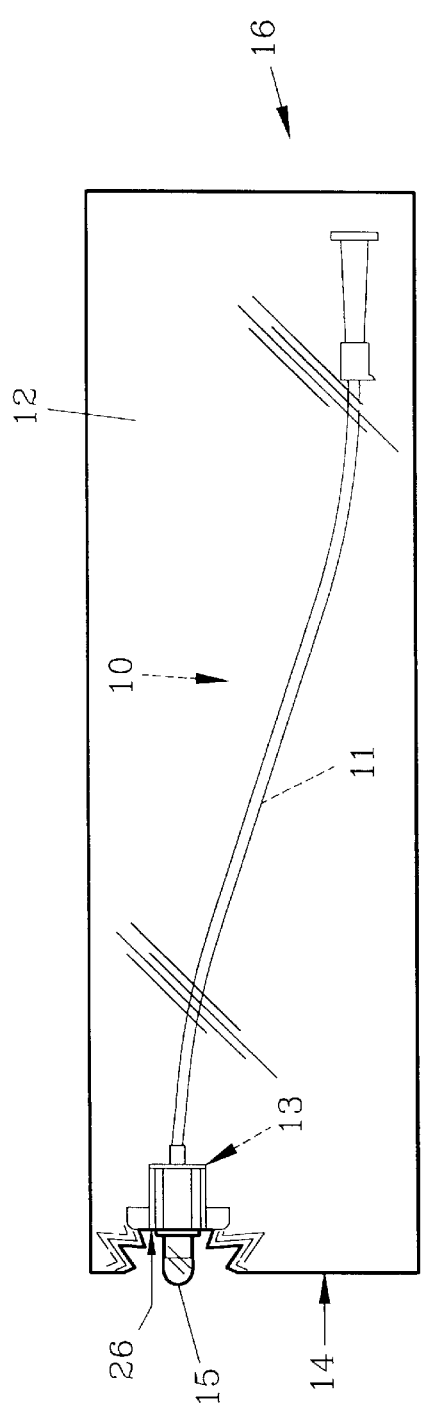

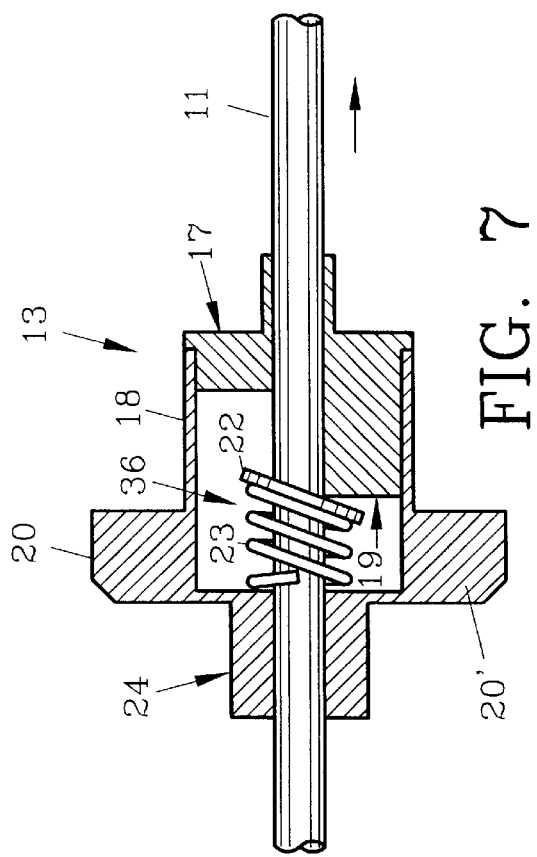
FIG. 7
FIG. 5
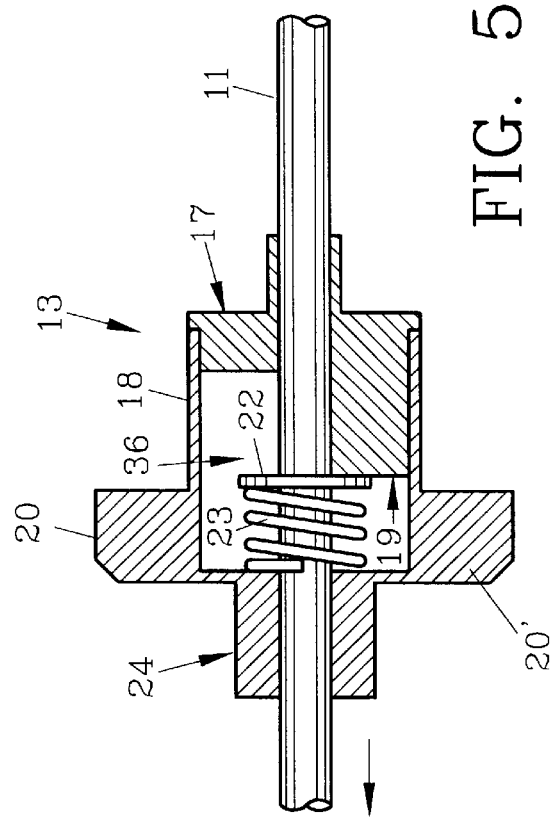
FIG. 8
FIG. 6

CATHETER MOVEMENT CONTROL DEVICE AND METHOD

FIELD OF THE INVENTION

The invention herein pertains to packaged catheters and particularly to control devices for limiting or controlling the extension of the catheter tube into and from the package.

DESCRIPTION OF THE PRIOR ART AND OBJECTIVES OF THE INVENTION

Various devices have been conceived in the past to limit or control the movement of catheter tubes into and out of its surrounding package to stop or retard the catheter tube movement. As such catheters have lubricants applied, it is often difficult to control the insertion of the catheter tube which is formed from a lightweight, flexible, polymeric material. Insertion techniques vary and the personnel involved must be aware that an obstruction encountered, in for example the urethral tract, must be recognized and precautionary steps taken. Otherwise, forcing the catheter tube into or through an obstruction may cause significant discomfort, the creation of false passages which may become infected, or may result in severe (or fatal) injury to the patient. An important objective is to achieve a movement control device that does not add any perceptible movement-retarding force while the catheter is being advanced. As such, the catheter tube must be manually inserted in increments to the desired depth for proper fluid drainage. However, a slight resistance during insertion caused by a curve or narrowing in the urethral tract can be overcome or transgressed by slight additional insertion force. It is desirable to minimize or eliminate manual touching of the catheter tube once it is extended from the sterile interior of the package. Contamination of the catheter tube can cause infections or the like to the patient and must be avoided.

Therefore, the present invention was conceived and one of its objectives is to provide a catheter movement control device which will allow movement therethrough in a forward direction and which will automatically terminate such movement in a rearward direction.

It is another objective of the present invention to provide a movement control device which will immediately capture the catheter tube when the advancing motion is discontinued to thereby instantaneously prevent any rearward motion of the catheter tube.

It is still another objective of the present invention to provide a movement control device which includes a housing defining a catheter tube channel therein.

It is yet another objective of the present invention to provide a catheter movement control device which includes a pair of wings on the housing that helps prevent axial housing rotation within the package.

It is a further objective of the present invention to provide a catheter housing containing a pivotable circular tube gripper and a resilient biasing means which is mounted on the catheter tube.

It is still a further objective of the present invention to provide a method of controlling the movement of the catheter whereby the catheter tube is manually directed through the control device in a forward direction and upon encountering resistance, the tube gripper pivots to engage the catheter tube to terminate rearward tube movement.

Various other objectives and advantages of the present invention will become apparent to those skilled in the art as a more detailed description is set forth below.

SUMMARY OF THE INVENTION

The aforesaid and other objectives are realized by providing a catheter movement control device contained within a standard flexible transparent package which includes a cylindrical housing formed from a suitable plastic which defines a catheter tube channel therewithin. Wings positioned on the outer sides of the housing help stabilize the housing to prevent axial housing movement within the catheter package. The catheter package provides a sterile environment for the catheter and a cap on the external housing fitting prevents contaminants from entering the catheter tube. In use, the movement control device is held by the user and the catheter tube is manually manipulated therethrough for insertion into the urethra. Continued forward motion allows the catheter tube to penetrate deeper into the urethra. If resistance is met during insertion, the catheter tube is prevented from substantial rearward movement by the control device. The control device includes a biasing member which holds a tube gripper against a shoulder within the housing. If the catheter tube is urged rearwards, the tube gripper pivots against the shoulder to thereby engage the catheter tube with its radially aligned teeth instantly preventing the catheter tube from such rearward movement. Once the resistance has ceased, the catheter tube again can be moved forwardly through the housing and out of the package a desired depth into the urethra for bladder drainage. Such drainage can be directed into the catheter tube package or, the catheter tube package can be opened at its rear end to act as a conduit for conducting such fluids to a commode or other satisfactory receptacle.

BRIEF DESCRIPTION OF THE DRAWINGS

FIG. 1 illustrates the invention as contained within a conventional catheter package;

FIG. 2 demonstrates the catheter package of FIG. 1 but with the catheter tube partially extended therefrom;

FIG. 5 features a partial cross-sectional view of the catheter control device containing a catheter tube with the biasing member in a more compressed posture;

FIG. 6 demonstrates the biasing member and catheter tube as seen in FIG. 5 but enlarged and in a cross-sectional representation;

FIG. 7 illustrates a partial cross-sectional view of the control device with the catheter tube as urged in a rearward direction with the biasing member extended and the tube gripper pivoted;

FIG. 8 shows an enlarged view of the biasing member and tube gripper engaging the tube in a cross-sectional representation as seen in FIG. 7.

DETAILED DESCRIPTION OF THE PREFERRED EMBODIMENT AND OPERATION OF THE INVENTION

Figure 3:
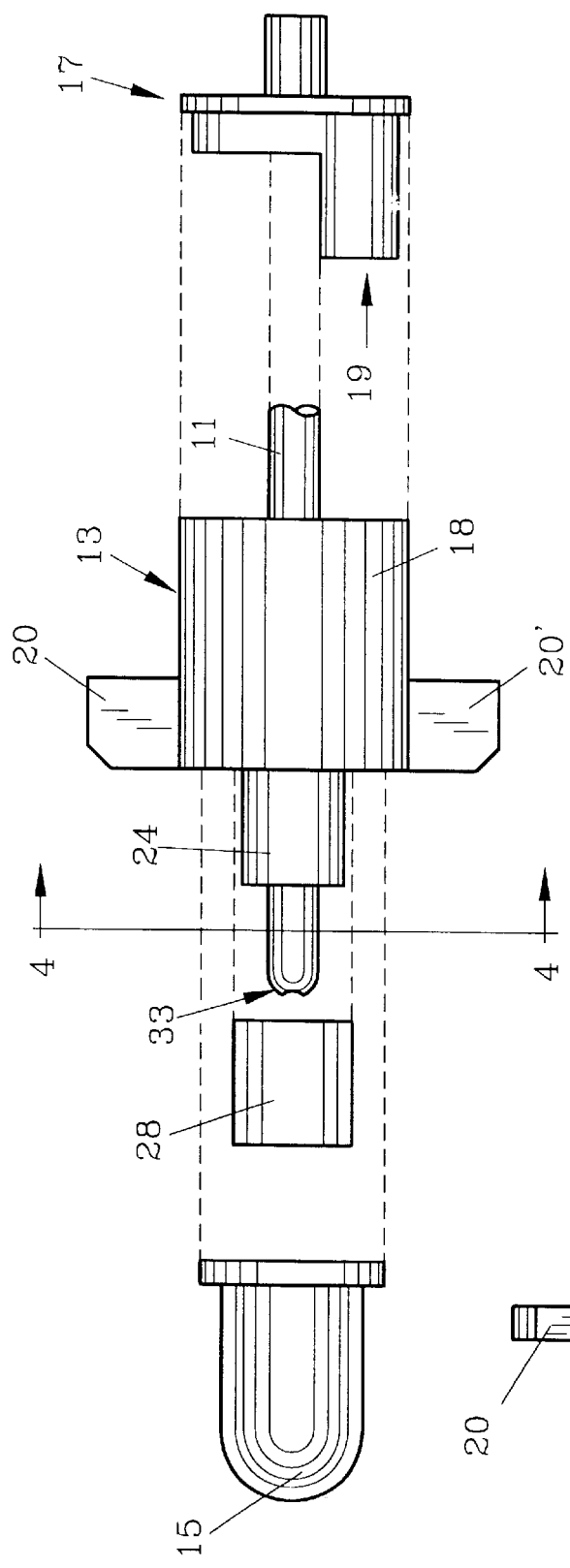
FIG. 3 shows an enlarged side view of the catheter movement control device in an exploded fashion and removed from the catheter package.
Figure 9:
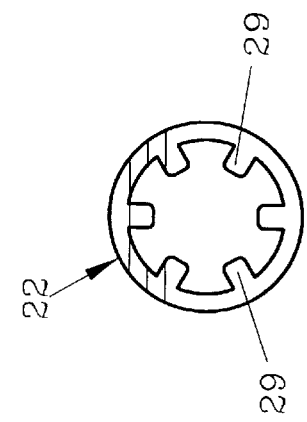
FIG. 9 is a front elevational view of the tube gripper as shown in FIG. 6 but removed from the catheter tube.

For a better understanding of the invention and its method of use, turning now to the drawings, FIG. 1 demonstrates preferred urethral catheter 10 contained within conventional transparent, polymeric package 12 having an application or front end 14 and a rear end 16. Catheter package 12 has front and back sides which are attached or sealed around the perimeter thereof to form a pocket for containing catheter 10. Catheter 10 includes catheter tube 11 which is formed of a conventional polymeric material and which passes through catheter movement control device 13. Cap 15 as seen in FIGS. 1 and 3 prevents contamination of tip 33 of catheter tube 11 as shown in FIG. 2. As would be understood, catheter tube 11 is manually manipulated into the urethra from package 12, outwardly through opening 26 in package 12 which is sealed around fitting 24.

Figure 4:
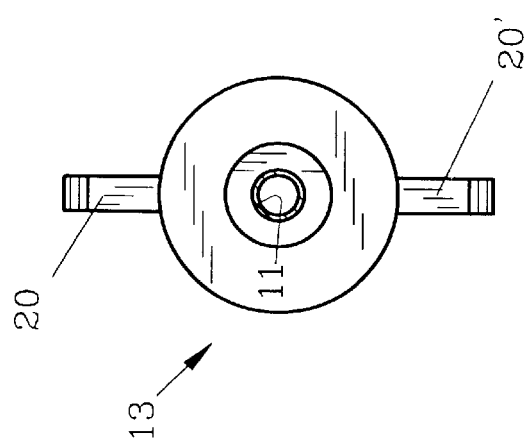
FIG. 4 depicts a front view of the catheter movement control device as shown in FIG. 3 along lines 4—4.

In FIG. 3, partial catheter tube 11 is shown in preferred movement control device 13, with rear section 17 exploded therefrom. Rear section 17 engages control device housing 18 and includes shoulder 19 as will be described in more detail below. As further understood, attached to or integrally formed with movement control device 13 are wings 20, 20' (shown in FIGS. 3 and 4) which assist the user in holding control device 13 in package 12 during manipulation of catheter tube 11 therethrough. Catheter tube 11 passes forwardly (right to left in FIG. 3) through movement control device 13 with tube gripper 22 and coil spring biasing member 23 mounted thereon. Cylindrical fitting 24 of movement control device 13 projects through opening 26 in package 12 (FIGS. 1 and 2) and is held securely in place by polymeric collar 28. Cap 15 covers the end of tip 33 of catheter tube 11 and prevents contaminant entry into tip 33 and catheter package 12. Wings 20, 20' are shown which stabilize cylindrically shaped control device 13 within catheter package 12 and prevent axial movement thereof.

In FIGS. 5, 6, 7 and 8 catheter movement control device 13 is shown in partial cross-sectional view with housing 18 assembled (FIGS. 5 and 7) with rear section 17 in engagement therewith. Rear section 17 may be glued in tight, frictional engagement, sonically welded or integrally formed with housing 18. Catheter tube 11 passes through tube channel 36 defined by housing 13 and has mounted thereon biasing member 23 and gripper 22. As seen in FIG. 5, catheter tube 11 is being extended in a forward direction, outwardly from catheter package 12 (also seen in FIG. 2) through fitting 24 which may be integrally formed such as by molding, with housing 18. Biasing member 23 which preferably is a lightweight metal coil spring, although other type and shapes of biasing members could be used such as leaf springs, or resilient collars formed of rubber or elastic materials. As catheter tube 11 moves in a forward direction (right to left as shown in FIG. 5) biasing member 23 is in a somewhat compressed state while gripper 22 changes its angulation by pivoting counter-clockwise about the flat edge of surface 19, thereby permitting the catheter tube to slide freely past gripper teeth 29. As catheter tube 11 is moved in a rearward direction, left to right as shown in FIGS. 7 and 8, biasing member 23 expands, thereby urging tube gripper 22 into contact with shoulder 19. As shoulder 19 only contacts the lower portion of tube gripper 22, tube gripper 22 pivots as seen in FIGS. 7 and 8 to thereby deflect and tightly grip catheter tube 11, preventing further rearward catheter tube 12 movement, except if substantially greater forward urging were employed for tube 11.

FIG. 6 demonstrates the position of tube gripper 22 on catheter tube 11 (seen in cross section) in its adopted or upright position as to allow catheter tube 11 to move forwardly, freely through control device 13 without restriction. Teeth 29 are also shown in FIG. 6 contiguous to tube 11 but do not restrict its movement. In FIG. 7, tube gripper 22 is slanted or biased causing teeth 29 as shown in FIG. 8 to deflect and grab catheter tube 11, thereby restricting and preventing rearward movement of catheter tube 11.

The preferred method of controlling the movement of a catheter such as catheter 10 as shown in FIGS. 1 and 2 with catheter tube 11 contained within catheter package 12 includes the steps of: first, removing cap 15 from catheter control device 13. Next, catheter tube 11 is manually urged through control device 13 in a forward direction thereby extending catheter tube 11 from package 12 where it can then be easily inserted into the urethra. Catheter tube 11 can thus be continually extended a desired length. Should resistance be sensed during the extension and insertion, the forward motion of catheter tube 11 may stop. If such resistance is large, catheter tube 11 will thus be urged rearwardly, and as additional sufficient manual force applied, catheter tube 11 will slide past biased tube gripper 22. Large resistance as explained will cause biasing member 23 to expand, forcing tube gripper 22 against shoulder 19 within control device housing 18. Manual force is applied as tube gripper 22 pivots, deflecting and engaging flexible catheter tube 11, rearward motion of catheter tube 11 will stop. Should relatively slight resistance occur from navigating a curve in the urethral tract, it may be overcome by additional forward urging of catheter tube 11. Once the resistance subsides biasing member 23 will relax and tube gripper 22 will again return to a slanted posture against surface 19. Catheter tube 11 can thereagain be manually urged forward for deeper penetration into the urethral tract. Once catheter tube 11 is sufficiently positioned in the bladder, drainage will occur as usual.

The illustrations and examples provided herein are for explanatory purposes and are not intended to limit the scope of the appended claims.

I claim:

1. A catheter movement control device comprising: a housing, said housing defining a catheter tube channel for containing a catheter tube, a tube gripper, said tube gripper pivotally mounted within said housing contiguous said catheter tube whereby said tube gripper allows said catheter tube to move through said housing in a forward direction and prohibits movement of said catheter tube through said housing in the opposite direction.

2. The catheter movement control device of claim 1 wherein said tube gripper is circular.

3. The catheter movement control device of claim 2 wherein said tube gripper comprises a tooth, sand said tooth extends radially.

4. The catheter movement control device of claim 2 wherein said tube gripper comprises a plurality of teeth.

5. The catheter movement control device of claim 1 further comprising a biasing member, said biasing member contiguous said tube gripper.

6. The catheter movement control device of claim 5 wherein said biasing member comprises a spring.

7. A catheter movement control device for receiving a catheter tube, said control device comprising: a housing, said housing defining a catheter tube channel therewithin, a tube gripper, said tube gripper for mounting on a catheter tube contained within said channel, a biasing member, said biasing member contiguous said tube gripper to bias the same along the catheter tube, said tube gripper pivotal to allow a catheter tube to move in a forward direction through said housing and to prohibit movement through said housing in a rearward direction.

8. The catheter movement control device of claim 7 further comprising a catheter package, said catheter package enclosing said catheter movement control device.

9. The catheter movement control device of claim 7 wherein said tube gripper is circular.

10. The catheter movement control device of claim 9 wherein said tube gripper comprises a tooth.

11. The catheter movement control device of claim 10 wherein said tooth is radially positioned.

12. The catheter movement control device of claim 7 wherein said biasing member comprises a coil spring.

13. A catheter movement control device comprising: a housing, said housing defining a catheter tube channel for containing a catheter tube, a tube gripper, said tube gripper contained within said housing contiguous said catheter tube, a biasing member, said biasing member contiguous said tube gripper, whereby said tube gripper allows said catheter tube to move through said housing in a forward direction and prohibits movement of said catheter tube through said housing in the opposite direction.

14. The catheter movement control device of claim 13 wherein said biasing member comprises a spring.

* * * * *